United States Patent [19]
Mayer

[11] Patent Number: 5,871,017
[45] Date of Patent: Feb. 16, 1999

[54] RELATIVE MOTION CANCELLING PLATFORM FOR SURGERY

[76] Inventor: Paul W. Mayer, 6290 SW. 92nd St., Miami, Fla. 33156

[21] Appl. No.: 950,772

[22] Filed: Oct. 15, 1997

[51] Int. Cl.⁶ .................................................. G09B 23/28
[52] U.S. Cl. ............................ 128/897; 128/923; 607/17; 607/3; 607/9; 269/236; 269/297
[58] Field of Search ..................................... 128/897, 923, 128/924, 899; 607/3, 9, 17; 269/236, 297

[56] References Cited

U.S. PATENT DOCUMENTS

| | | | |
|---|---|---|---|
| 2,925,814 | 10/1960 | Vibber et al. | |
| 4,051,841 | 10/1977 | Thoma | 600/510 |
| 4,804,054 | 2/1989 | Howson et al. | |
| 4,899,730 | 2/1990 | Stennert et al. | |
| 5,016,642 | 5/1991 | Dukes | 128/696 |
| 5,276,429 | 1/1994 | Cadossi et al. | |
| 5,443,077 | 8/1995 | Krogh et al. | |
| 5,603,321 | 2/1997 | Kynor | 128/901 |
| 5,692,907 | 12/1997 | Glassel | 434/262 |
| 5,727,552 | 1/1996 | Ryan | 128/899 |

FOREIGN PATENT DOCUMENTS

| | | |
|---|---|---|
| 0456103 | 11/1991 | European Pat. Off. |
| 2352026 | 4/1975 | Germany. |
| 9410964 | 10/1994 | Germany. |
| 9501757 | 1/1995 | WIPO. |

OTHER PUBLICATIONS

T. Acuff et al., "Minimally Invasive Coronary Artery Bypass Grafting", The Society of Thoracic Surgeons, vol. 61, pp. 135–137, 1996.

Calafiore, Antonio M. et al., "Minimally invasive coronary artery bypass grafting.", Ann. Throac. Surg., vol. 62, pp. 1545–1548 (1996).

Greenspun, Harry G., et al., "Minimally invasive direct coronary artery bypass (MIDCAB): Surgical techniques and anesthetic considerations.", Jour. Cardio. Vasc. Anesth., vol. 10, No. 4, pp. 507–509 (1996).

Hartz, Renne S., "Minimally invasive heart surgery.", Circulation, vol. 94, No. 10, pp. 2669–2670 (1996).

Winslow, Ron., "Hope and hype follow heart–surgery method thats easy on patients.", Wall Street Journal, front page, Teusday, Apr. 22, 1997.

Mehta, Stephanie N., "Robotics may spur less–invasive surgery.", Wall Street Journal, Maketplace section, p. 1, Thursday, Jun. 19, 1997.

*Primary Examiner*—Gene Mancene
*Assistant Examiner*—Ira Hatton

[57] ABSTRACT

An apparatus for open-heart surgery includes a platform (20) to support the surgeon's hand (or an instrument) and a cam (30) for reciprocating the platform oscillation around a hinge (12). The cam is shaped so that the pattern of the platform oscillation follows the beating heart's motion. The platform motion triggers a momentary-contact switch on each cycle. The switch drives a pacer, which paces the heart to beat in synchrony. The platform rate is set slightly above the un-paced heart beat rate; this keeps the heart in close synchrony with the platform oscillation and stabilizes its motion. The platform and heart move together, relative motion is canceled, and the surgeon need not compensate. The platform is mounted (10) on an adjustable support and a laser beam is used to angularly align the platform to the heart oscillation. A capacitive sensor (21) detects the heart-to-platform distance, which is used to generate an audible tone proportional to the distance; the tone is used to adjust the platform oscillation amplitude and/or phase for minimum variation of the heart-platform distance.

28 Claims, 5 Drawing Sheets

RELATIVE MOTION CANCELLING PLATFORM FOR SURGERY

CROSS-REFERENCE TO RELATED APPLICATIONS

The present application is a non-provisional application claiming benefit under 35 U.S.C. §119(e) of provisional application no. 60/047,349, filed May 21, 1997, and 60/028,395, filed Oct. 15, 1996, the entire contents of both of which are hereby incorporated herein by reference.

FIELD OF THE INVENTION

The invention relates to a hand-supporting platform for surgery. More specifically, it relates to a platform moving in synchronization with a surface of a moving organ, such as the heart, so that the surgeon can more easily operate at that surface.

BACKGROUND OF THE INVENTION

In many surgical operations work must be done on a moving organ, such as a beating heart. This requires not only manipulations to perform the operation which would be required in any case (even if the organ were still), but also requires correction of the surgeon's hand motions to compensate for the organ motion so as to keep the surgeon's hands still relative to the work area.

One such operation which has recently been gaining in popularity is known as minimally invasive coronary artery bypass grafting. As described by Calafiore et al, "Minimally invasive Coronary Artery Bypass Grafting", Ann. Thorac. Surg., 62:1545–1548 (1996), minimally invasive coronary artery bypass (MICAB) is defined as an intervention that does not require median sternonomy or the use of cardiopulmonary bypass (CBP). The incision in the chest wall is small, and the aorta, in any portion, is not the direct source of inflow of blood supply to the bypass grafts. MICAB promises to become an important addition to the surgical treatment of coronary artery disease.

In this technique, the patient is anesthetized and intubated with a single endotracheal tube and hemodynamic monitoring. Short-acting anesthetic agents are used, as extubation of the patient in the operating room is routine. The chest is opened through a fourth or fifth intercostal space incision and the pericardium is opened longitudinally. The left anterior descending coronary artery (LAD) is identified and inspected. The LIMA is harvested through the same incision with or without the aid of a thoracoscope. One or more costal cartilages may be resected to achieve better visualization and dissection of the full length of the LIMA. The artery can be harvested as a pedicle or as a skeletonized vessel.

The patient is heparinized (1 mg/kg), and diluted papaverine is injected into the pedicle and intraluminally into the LIMA through a blunt-tipped cannula. Traction sutures are applied to the edges of the pericardium. After selection of a site for construction of the anastomosis and assessment of the length of the LIMA, distal and proximal control of the LAD is required. A snare of 4/0 PROLENE (Ethicon, Somerville, N.J.) or silicone suture can be applied proximally and distally to the site selected for the anastomosis. Alternatively, the vessel can be opened and a FLOW-RESTER placed intraluminally. The surgical blower (VISUFLOW, Research Medical, Midvale, Utah) is used for visualization. Electrocardiographic changes, arrhythmias, and ventricular fibrillation are rare events during occlusion of the LAD. Traction sutures can be applied to the visceral pericardium lateral to the LAD, thereby allowing for better stabilization of the artery. Alternatively, a suction device (Medtronic Inc, Minneapolis, Minn.) or a stabilizer (CTS Inc) can be used. Short-acting β-blockers or calcium channel blockers are used to reduce heart rate when necessary.

The LAD to LIMA anastomosis is performed using a 7/0 or 8/0 running PROLENE suture, either as a single suture or as two strategically placed sutures at the toe and heel of the LIMA. Some surgeons prefer interrupted sutures. At completion of the anastomosis, heparin is reversed with protamine sulfate. Closure of the chest is as in any standard thoracotomy, leaving a pleural tube for drainage. An intrapleural catheter is placed for pain control. The patient is extubated in the operating room or shortly thereafter. Patency of the artery is confirmed by standard Doppler (velocity) echocardiography intraoperatively and by duplex scanning of the LIMA early and late postoperatively in every patient. This is usually done 2 to 3 hours postoperatively and 24 hours after operation. Diastolic flow predominates in a patent LIMA. Most centers report early discharge from hospital and significant cost savings associated with this procedure.

It has been reported that by mid-1996 at least 200 MICAB procedures had been performed in various universities and private hospitals in the United States and several hundred more in Europe and South America (Hartz, "Minimally Invasive Heart Surgery", Circulation, 94:2668–2670 (1996)). For other respects about such surgery, see also Calafiore et al, "Left Anterior Descending Coronary Artery Grafting Via a Left Anterior Small Thoracotomy Without Cardiopulmonary Bypass", Ann. Thorac. Surg., 61:1659–1665 (1996); Stanbridge et al, "Minimal-Access Surgery for Coronary Artery Revascularization", Lancet, 346:837 (1995); Acuff et al "Minimally Invasive Coronary Artery Bypass Grafting", Ann. Thorac. Surg., 61:135–137 (1996), and Subramanian et al "Minimally Invasive Coronary Artery Bypass Surgery: A MultiCenter Report of Preliminary Clinical Experience", Circulation, 92 (Suppl. 2):645 (1995).

While such operations have been successfully performed in many different centers, substantial risks are involved in performing surgery on a beating heart. In such operations the arteries are small, the stitches fine, and the sutures are liable to rip due to the heart motion. The risk to the patient is considerable. There have been cases in which the arterial walls were ripped, requiring the operation to be aborted and causing complications.

At first blush it might appear that the heart's motion, being regular, could be easily compensated for by the surgeon. However, the heart motion amplitude is about a half inch (1.3 cm), and this is quite large compared to the precision required of the surgeon's manipulations. The rhythm is erratic. The motion tends to sudden pulsations rather than a smoothly-varying motion such as a sinusoidal motion.

Thus, the acceleration of the heart surface changes rapidly. During the intervals of high acceleration the surgeon is substantially unable to do anything beyond keeping the instruments near their positions relative to the heart, so that no suture rips or unintended punctures occur. The operation is actually performed intermittently during the lulls of low acceleration.

Because of these difficulties, the heart is often artificially slowed down during operations, as discussed above, such as by means of short acting β-blockers or calcium channel blockers. This improves the surgeon's situation in proportion to the change in rate, but for obvious reasons the degree of improvement is limited.

Moreover, the heart (like most organs) responds to stimulation. A suture needle prick often causes this muscular organ to twitch strongly, which is very difficult to compensate for. Twitching will not be lessened by slowing the heart down.

Calafiore et al, supra, report that stabilization of the heart during construction of the anastomosis is an important aspect of the procedure, and devices are being developed that will aid the surgeon during this critical part. However, physically immobilizing the heart is a less than desirable technique as it could damage the heart or impair circulation during this period.

Devices for surgery on a beating heart were reported in a front-page story in the Wall Street Journal of Apr. 22, 1997. The story said that CardioThoracic Systems, Inc. is marketing a device resembling a two-pronged fork which is pressed against the beating heart to stabilize the pressed region and allow the surgeon to operate. The cost is $1850 per operation. Another device sold by Medtronic is called the "Octopus"; it costs $10,000. Others are expected to be marketed soon by Baxter Inc. and U.S. Surgical Corp.

The CardioThoracic system can only be used in about 20% of all bypass operations, according to the article. Triple and quadruple bypass and valve repairs require stopping the heart.

Pressing on the heart naturally will affect the blood flow through it, and the amount of pressure is limited. The problem of twitching is not overcome, and it appears that the heart surface cannot be immobilized completely.

The new devices "set off intense debate over safety and economics", according to the article. "Some surgeons are particularly skeptical that joining tiny blood vessels on the surface of the heart can be done as successfully while the heart is beating—the CardioThoracic way—as when it is stopped. . . . During a recent [stopped-heart] operation, Dr. Colvin [of New York University Medical Center] peered through magnifying goggles as he performed the delicate task of joining the replacement vessel to a coronary artery, using a tiny needle and barely visible sutures. 'At this point, if you're doing it "beating-heart" you're cursing a mile a minute', he remarked."

The article also reported on a stopped-heart kit which is being aggressively marketed in competition with the CardioThoracic device. Produced by Heartport Inc., [is] it costs $5000 per kit. It has been used in about 500 cases. Like the CardioThoracic method, the Heartport method avoids opening the ribcage, instead using a smaller opening. Because opening the ribcage is a traumatic and painful operation, patients are more likely to chose an operation which requires only a smaller opening.

However, the Heartport method involves stopping the heart with a balloon in the aorta and drugs, and using a heart-lung machine to keep the patient alive during the operation.

The article noted that stopping the heart is stressful and dangerous, and is impossible if the patient is too sick. The cost of using the heart-lung machine is as much as $2,300 (the machines cost about $150,000) and about 6% of patients suffer complications, including stroke, depression, and severe infections. The ideal heart operation would need only a small incision, like the Heartport and CardioThoracic operations; avoid the expense and risk of a heart-lung machine, like the CardioThoracic operation; and stop the heart so the surgeon can safely operate on the delicate arteries, as in the Heartport operation. None of the available operations or devices achieve all these.

The prior art has not solved these problems of working on a moving organ, despite the great need for improvement.

SUMMARY OF THE INVENTION

Accordingly, the present invention has an object, among others, to overcome deficiencies in the prior art such as noted above.

The present invention provides a hand-supporting platform which is driven by a specially-shaped cam to move up and down in synchronization with the surface of the heart (or other organ or part). The heart's motion is effectively canceled (or, virtually stopped) relative to the platform. The surgeon's hand, at rest relative to the platform, is also effectively at rest relative to the heart and delicate operations can be performed with much more ease, and much less risk, than formerly.

The invention, in particular embodiments, includes specific mechanisms to eliminate the relative motion of the moving anastomotic target and the platform, as discussed below. However, the platform is not actually at rest. The platform mimics all the accelerations of the heart surface, and the surgeon must resist the acceleration forces on his or her hand in order to keep the hand stable relative to the platform. The surgeon's fore-arm rests on the moving platform but the operating hand must dangle at least in part over the end of the platform in order that the surgeon may work. It would be thought that the platform's rapid motion might cause the surgeon's hand to flail, and the instrument held in the hand to swerve. Unexpectedly, this does not happen.

On a mock-up of the invention, a person was able thread a fine needle moving up and down at up to 150 "beats" per minute while resting his hand on a platform moving synchronously. This would have been impossible if the person's wrist had been limp and his hand flailing during the threading operation.

It appears that one mechanism to overcome hand acceleration is tensing opposing muscles, which makes the hand rigid enough to prevent flailing. Tensing can be done without conscious thought and it will not distract the surgeon from the operation.

Nor does tensing impair dexterity. This can be easily verified by tensing the muscles to push fingertips together so forcefully that the tensed hand does not deflect from the fore-arm when its wrist hand is struck. It will be found that the fingers can still be readily moved without relaxing the tension.

If the fingers are held together only loosely in the same position, they flail briefly when the wrist is struck, especially if struck without any warning.

It is to be noted that tensing does not require any thought and requires only slightly more effort than if both the heart and the hand were actually at rest. Mutual tensing is a natural process in the body since making the limbs rigid is required in many normal activities, and in fact the nervous system can tense almost the entire body at once; this is done by weight-lifters in muscle display contests. It is also possible that the nervous system automatically compensates for hand accelerations by activating just one muscle of an opposing pair. Since hand acceleration occurs in almost all arm movements and mutual tensing is wasteful of energy, this would not be surprising.

Whatever the reasons, the hand accelerations caused by the present invention are easily and precisely compensated for without undue effort.

Thus, the surgeon's main problem in prior-art minimally invasive cardiac surgery—the hand-eye coordination problem of compensating for the heart's motion—is overcome. The only remaining difficulties, keeping the hand rigid relative to the platform and fore-arm and focussing the eyes on the moving surface, are relatively minor.

The present invention provides a dramatic advance in the art which will not only save time and energy but also lives; and the invention accomplishes this advance with an apparatus whose simplicity, low cost, and reliability are very unusual in the medical field.

Rather than driving the platform according to the heart's motion, which would require complex electronics, sensors, and servo-motors, the present invention preferably drives the heart according to the platform's motion. This innovation allows the platform to be driven by a simple cam and motor mechanism.

The heart is paced by electric signals timed to the oscillations of the platform, as detected by a simple momentary-contact switch which is closed once in each oscillation of the platform. The switch may be closed by the platform itself or by a cam. Switch closure (or opening) generates a trigger pulse to conventional pacer circuitry, which may provide for an adjustable delay between the trigger pulse and the heart stimulus. Electronic and/or mechanical means to adjustably advance or retard the pacing signal can be used.

The paced heart rate avoids the twitchiness problem mentioned above, in which the heart muscle moves unexpectedly when touched or pricked. The heart is preferably triggered at a rate slightly above the heart rate to which the heart has been slowed to naturally heat without pacing. It has been found that when the heart is driven at a slightly higher rate, twitchiness is eliminated. Because the present invention is able to easily compensate for heart motion regardless of the beating rate, the operation becomes easier when the heart is paced to beat faster than would otherwise be the case.

Pacing the heart also improves the regularity of the beats and stabilizes the heart oscillation amplitude, because blood flows into the heart chambers at constant rate and if the filling time for two beats is identical, then so will the amount of blood pumped on those beats be identical, and hence also the amplitudes.

Because the heart's motion is non-sinusoidal (as noted above), the present invention uses a rotary cam, driven by an ordinary electric motor, to oscillate the platform from full systole to full diastole. The cam profile is adjusted to match the heart's surface motion. In a preferred embodiment, the platform is hinged to a base and the cam position is adjustable relative the hinge position to adjust the amplitude of the platform motion for different sizes of heart. However, for a particular operation, the same cam can be used for all patients. Of course, the cam may be interchangeable for different profiles, if needed.

The lobed cam may be replaced by an equivalent of more general motion capability, such as an electrically-controlled actuator driven according to a voltage, digital signals, or the like, and having a pattern that is adaptable to different heart motion amplitudes, phases, or patterns.

To adjust the excursion (oscillation amplitude) and optionally also the synchronization (pacer timing advance or retard), the present invention employs another simple but effective innovation. The heart is, of course, a conductor of electricity, and the platform may easily be made of metal or to include a metal plate. Thus, a capacitor is formed between the heart and the platform, and the capacitance of this capacitor will vary with the heart-platform distance. [Since an] An electrical oscillating circuit is easily arranged to use the heart-platform capacitor as part of an LC circuit resonating in the audible range (or at a frequency that can be sub-divided to reach the audible range). Using conventional circuitry, power supply, and loudspeaker or earphone, the invention can provide an audible tone whose frequency is very nearly proportional to the heart-platform distance.

It is well-known that the ear can hear very slight frequency changes, and because of this a surgeon listening to the tone generated in the heart-platform capacitor circuit will be aware of heart-platform distance variations of less than one percent. Adjacent keys on the piano differ by six percent. The surgeon can then adjust the platform drive and/or the pacer electronics to minimize the frequency variation of the audible tone. When the platform is completely synchronized with the heart, then the tone will be flat, of constant pitch.

The platform oscillation is thus matched to the heart surface in oscillation profile, amplitude, and phase, which is a complete specification of the vibratory motion. However, the heart surface also has a displacement direction (generally, perpendicular to the heart surface) which can be accurately approximated as a straight-line motion. The platform also has a motion which is approximately linear. The end of the platform actually describes an arc if the platform is hinged, but this can be reduced by lengthening the hinged length of the platform or substituting another type of support. These two motion directions must be aligned, or the surgeon's hand will be jiggled side-to-side relative to the heart while it oscillates up and down.

To align the platform to the heart, the present invention uses yet another simple, reliable, and inexpensive device: a laser of the type used in pointers, costing less than one hundred dollars. The laser beam is set parallel to the motion of the platform end, where the surgeon's hand rests. With the platform at rest, the platform support is adjusted for position and angle while the surgeon watches the motion of the beam on the heart surface.

When the heart surface is moving perpendicular to the beam, the lateral location of the laser spot on the heart will be stationary, even though the beam spot moves in and out along the beam line. The displacement of the beam spot along the heart surface while the heart is beating will be zero. Conversely, if the heart surface is moving at an angle to the beam, the beam spot will traverse laterally across the surface, regardless of the angle which the heart surface makes with the beam. The sideways beam displacement will be readily apparent to the surgeon, sighting generally along the beam, and the platform support can easily be adjusted to set the platform oscillations parallel to the motion of the heart surface at the exact point where the surgeon wishes to operate.

The present invention solves a life-threatening problem which has not been even partially solved before, by eliminating relative motion between a moving organ and a surgeon's hand. The extreme simplicity of the invention is facilitated by the innovation of driving the heart to follow a mechanical oscillation. The consequent reliability, ease of use, and low cost are great advantages.

BRIEF DESCRIPTION OF THE DRAWINGS

The above and other objects and the nature and advantages of the present invention will become more apparent from the following detailed description of preferred embodiments taken in conjunction with drawings, wherein.

DETAILED DESCRIPTION OF THE PREFERRED EMBODIMENT

Here, and in the following claims:

"Platform" means any moving support, whether for a surgeon's hand or for a surgical instrument, alignment device, or sensor. A platform for supporting the hand and/or arm may be flat or contoured to the arm or hand, may have an outline shape adapted to support the hand, and may include wrist straps, arm brackets or hold-downs, or similar appliances.

"Synchrony", "synchronously", and related forms of this word mean at the same frequency, but not necessarily at the same amplitude, pattern, or phase.

Figure 1:
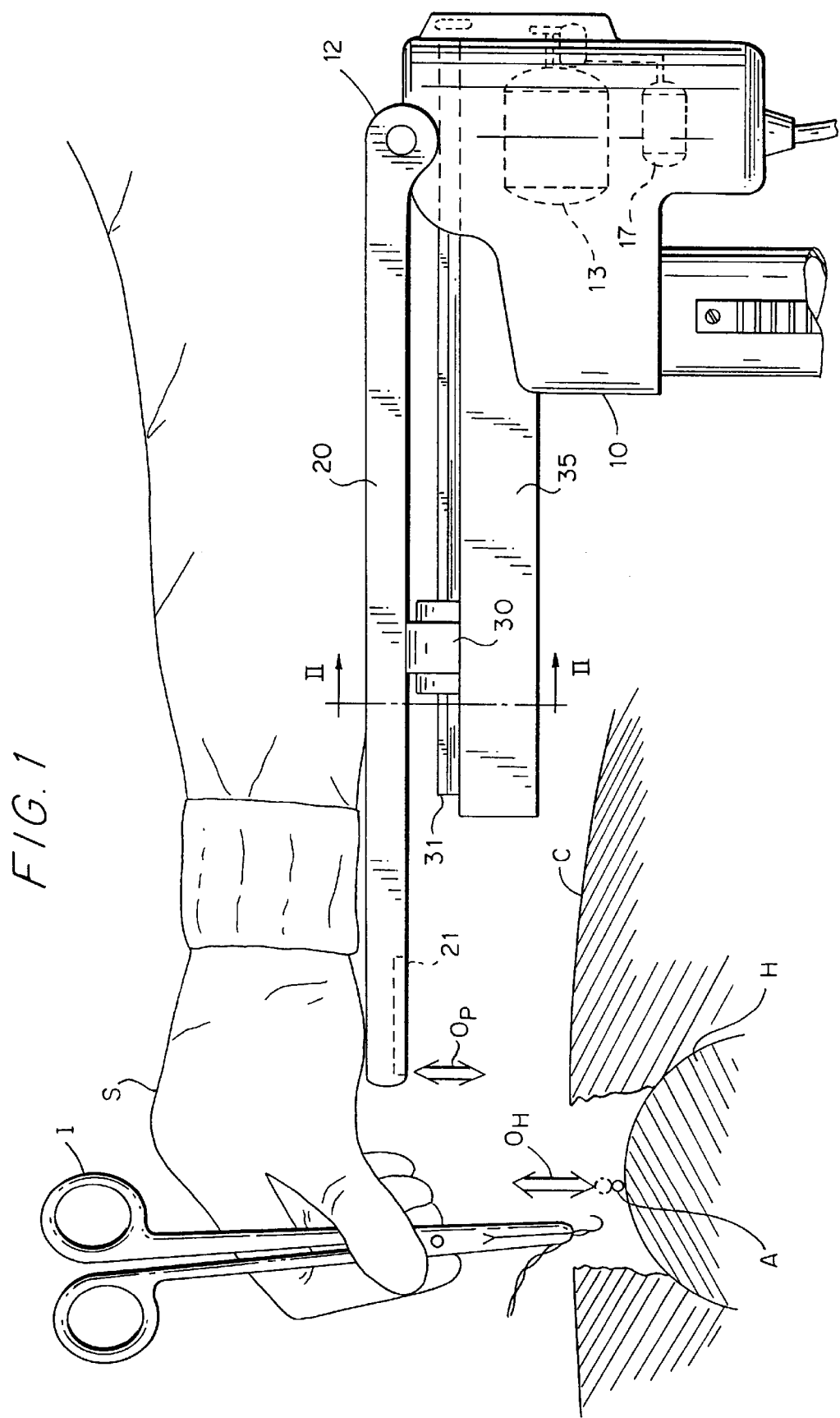
FIG. 1 is an elevational overview of the invention.

"Pattern" of an oscillation relates to the repeating shape of a graph of the oscillation as plotted against time. For example, if the displacement (in inches or centimeters) in a certain direction of one portion of the surface of a beating heart were to be graphed as a function of time, the graph over the period of one beat would be a pattern. Graphs could also be made of heart surface velocity or acceleration, and these also would represent patterns. The platform also will have a pattern. FIG. 1 shows the present invention in relation to a patient's chest C and heart H, which is being operated on by the hand of a surgeon S holding an instrument I. A coronary artery A, which is the site of the anastomosis, is shown on the surface of the heart H. The chest C and heart H are shown in cross section, but the invention and surgeon S are not.

The heart H is beating during the operation and its surface, and the artery A, are moving up and down in a heart oscillation $O_H$ which has a certain motion pattern (waveform), amplitude (displacement over one beat cycle), and frequency (beating rate).

The invention includes a platform 20 which moves up and down in a platform oscillation $O_P$ which mimics the heart oscillation $O_H$ in pattern, amplitude, and frequency. Because the platform oscillation $O_P$ follows the heart oscillation $O_H$, the surgeon S can easily operate on the moving heart. The platform oscillation $O_P$ is adjusted by mechanisms of the invention, as explained below, to cancel the relative motion between the surgeon S and a particular place on the heart H, such as for example the artery A.

The platform 20 is hinged to a base 10 by a hinge 12 and is driven into the platform oscillation $O_P$ by a rotating cam 30 which bears against the underside of the platform 20. The cam 30 is slidably but non-rotatably mounted on a cam shaft 31 which is rotated by a motor 13 mounted to the base 10 coupled to power and control circuitry (not shown in FIG. 1). The cam 30 profile is chosen so that the platform oscillation $O_P$ has the correct wave-form or temporal pattern of displacement, velocity, and acceleration (which is generally not a simple sinusoidal shape, although that is within the scope of the invention).

Figure 2:
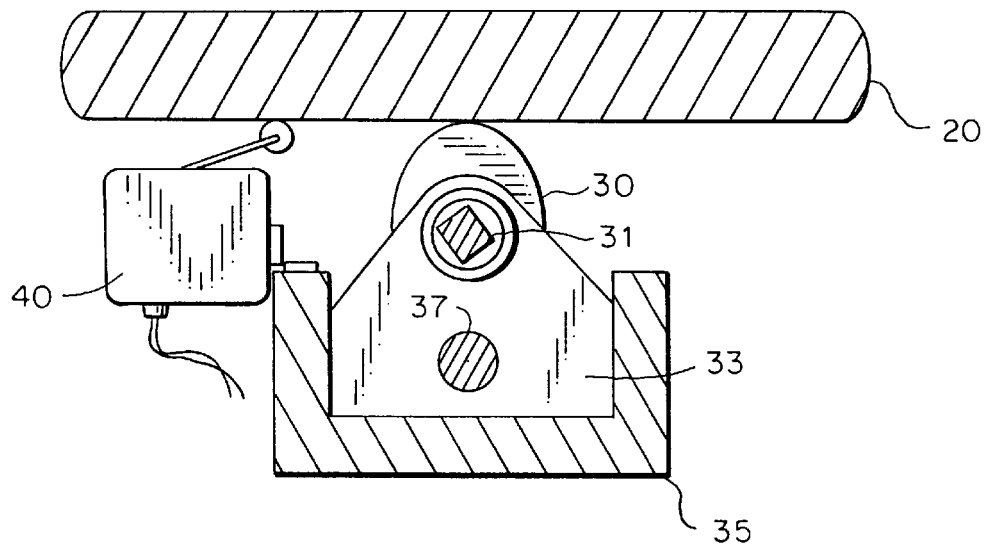
FIG. 2 is a sectional view along cross-section line II—II of FIG. 1.

The drive mechanism is shown in FIG. 2. The cam 30 bears against the underside of the platform 20 and pushes the platform 20 up and lets it fall down, so that the cam 30 and the platform 20 stay in contact. A positive-displacement cam system, or a pull-down return spring, not shown, is within the scope of the invention. However, the maximum downward acceleration of the platform is expected to be less than that due to gravity so that these would not ordinarily be needed to pull the platform 20 down.

The cam 30 may be molded of a strong, low-friction material such as nylon.

The profile of the cam 30, which matches the pattern of the platform oscillation $O_P$ to that of the heart oscillation $O_H$, is visible in FIG. 2. The cam surface appears as a curved line; this shape embodies the profile.

The cam 30 is driven by a cam shaft 31 which may be of square section to engage a square hole in the cam 30 (not visible in FIG. 2). The shaft 31 is supported in bearings in a slider 33, which moves in a channel 35 rigidly attached to the base 10. The amplitude of the platform oscillation $O_P$ is adjusted by moving the slider along the channel (in and out of the plane of the paper in FIG. 2) by means of a threaded rod 37 which engages a threaded hole in the slider 33. The threaded rod 37 is preferably driven by a motor 17 in the base 10 (shown in FIG. 1). A momentary-contact switch 40 is shown in FIG. 2, mounted on the channel 35. The switch 40 provides a trigger signal to a pacer (not shown in FIG. 2) which drives the heart to beat at a rate preferably slightly higher than when not paced. The switch 40 could also be mounted on the slider 33 or be incorporated into the base 10, for example in a triggering cam coupled to the driven end of the cam shaft 31. Any conventional trigger means is within the scope of the invention, including magnetic and optical triggers or triggers coupled to the drive circuits of the motor 13.

Figure 3:
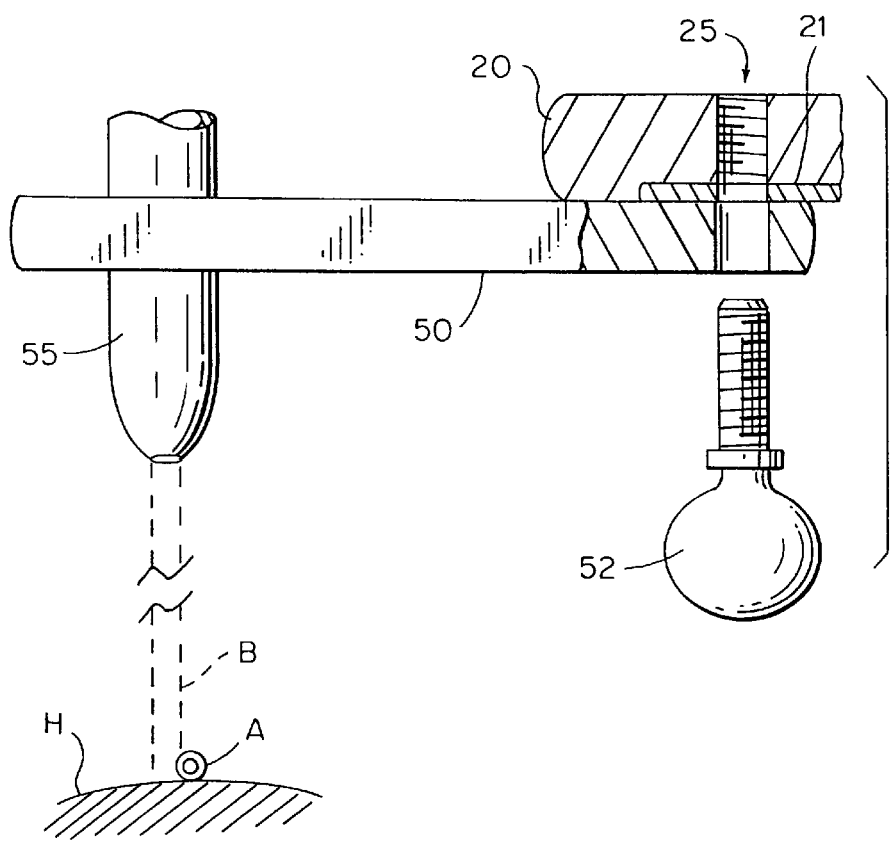
FIG. 3 is an elevational, partly cross-sectional view.

FIG. 3 shows the end of the platform 20 which oscillates with a laser 55 mounted in a clamp member 50 by means for attachment 52. The laser 55, which is preferably of the ordinary laser pointer type, emits a beam B which impinges on the heart H near the artery A which is to be operated on. The clamp member 50 is constructed so that the beam B is generally perpendicular to the axis of the hinge 12 and also the extension of the platform 20.

Figure 4:
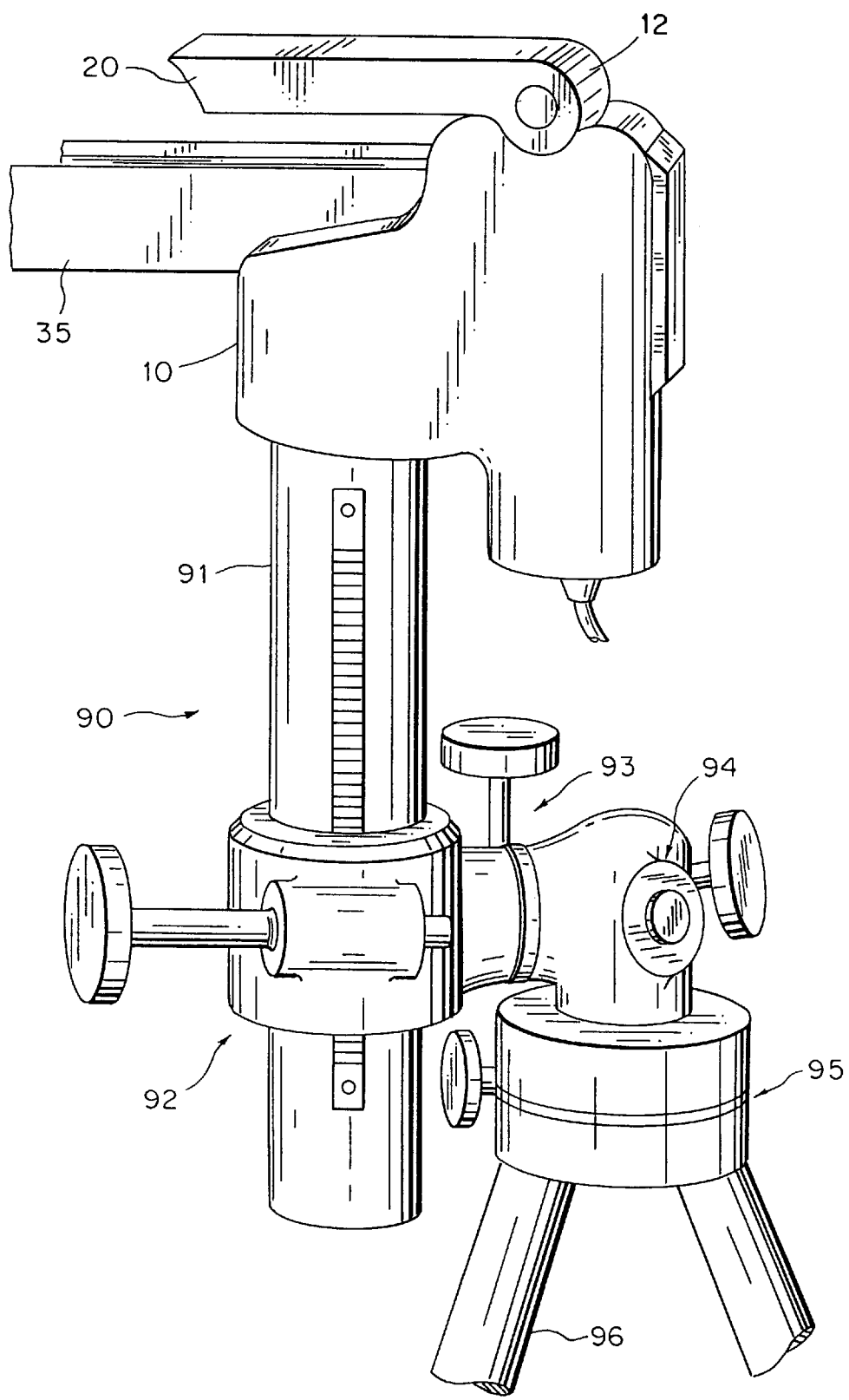
FIG. 4 is a perspective view of the base support.

The laser beam B is used to align the platform 20 to the heart oscillation OH (shown in FIG. 1). Referring now to FIG. 4, an adjustable multi-angle base support 90 is seen attached to the base 10, including longitudinally-extensible member 91 (for moving the platform 20 closer and farther from the heart H), longitudinal extension mechanism 92 (for example, the illustrated rack and pinion arrangement), and angular adjustments 93, 94, and 95 provided with suitable position/angle adjustments and/or clamps. The base support includes a tripod 96 or type of clamping arrangement for mounting to a surgical table, floor, or other stable object (not shown). The whole constitutes an arrangement for emplacing the platform adjacent the surface of the heart.

The platform is preferably not supported on the ribcage because the heart is more firmly fixed with respect to the backbone than to the breastbone; and thus the anterior surface of the heart does not partake in the breathing motions of the ribs. As the patient's back is stable in the course of the procedure, the apparatus of the present invention is preferably made immobile relative to the patient's back by affixing it to the floor or operating table. However, the present invention also comprehends mounting on the chest, ribcage, sternum, etc., when it is desired to also compensate for the patient's breathing motion.

Returning again to FIG. 3, since the base support 90 is able to adjust the laser beam B to any angle and any position on the heart, the beam B can be used to align the platform 20. To do this, the beam B position is brought to the area on the heart that is to be operated on, e.g., the artery A. The surgeon then watches for any sideways motion of the beam spot on the heart while it continues to beat. (The motor 13 is not powered and the platform 20 is still.) If there is no motion, then the beam B is aligned properly. The beam spot will of course move up and down along the beam line while the heart H is beating, but if the beam spot does not move across the surface then the platform oscillation $O_P$ and the heart oscillation $O_H$ will be aligned when the motor 13 is powered and there will be no relative sideways motion for the surgeon to contend with.

Instead of a laser, another sort of optical system could be used, including a telescope/microscope with cross hairs or a simple sight. Non-optical systems are also contemplated.

Once the platform 20 is properly aligned and the distance to the heart H is as desired, the base support is clamped and the motor 13 is powered to oscillate the platform. The surgeon then must adjust the motion of the platform so that the platform oscillation $O_P$ has the correct amplitude, phase, and frequency.

Figure 5:
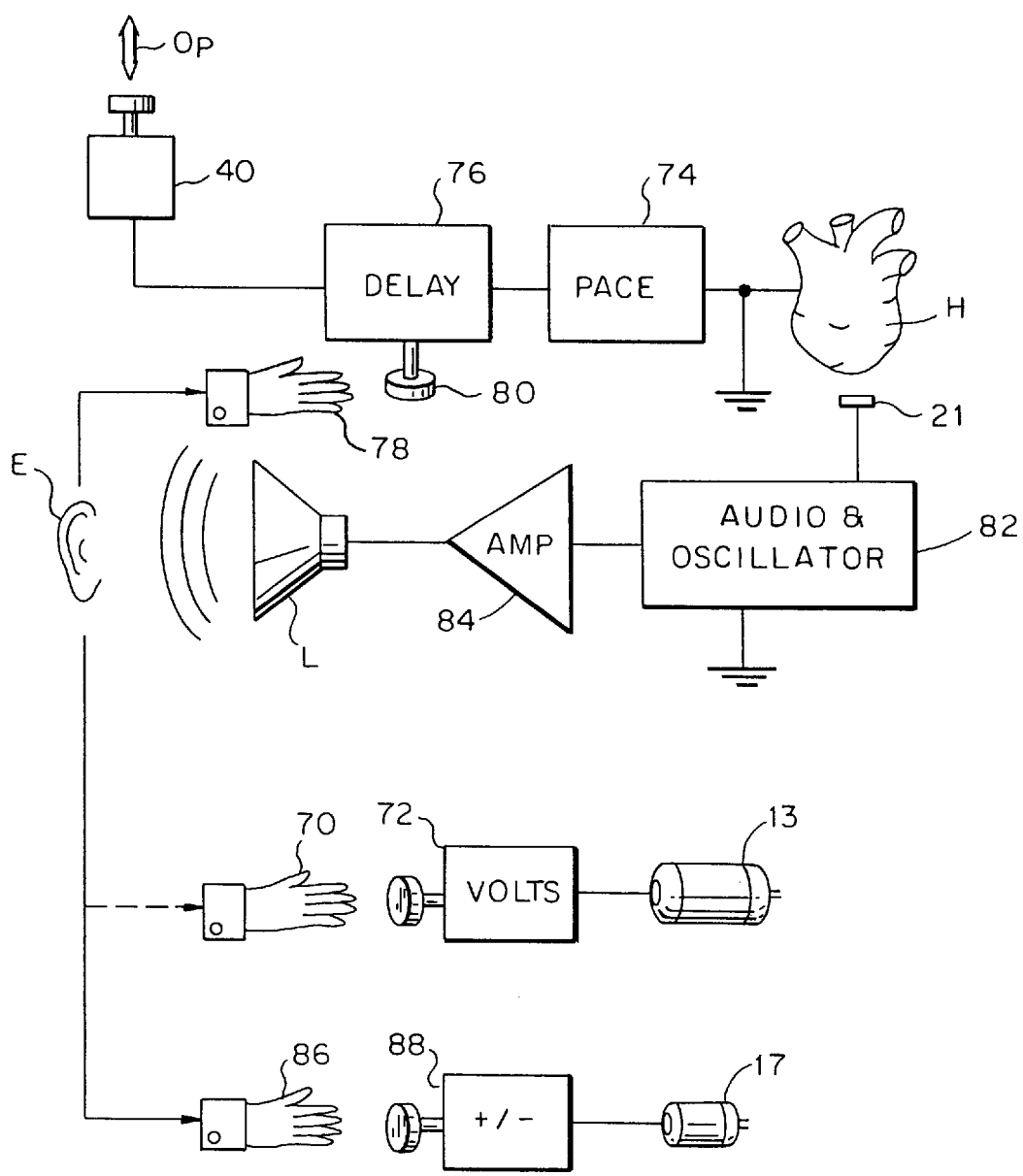
FIG. 5 is a schematic view of oscillation control.

FIG. 5 illustrates the control of these parameters. The surgeon first notes the heart rate without any pacing stimulus and then adjusts the volts applied to the motor 13 to set the platform oscillation rate slightly higher than that rate. The adjustment is illustrated schematically by a hand 70 and a knob 22. The pace circuitry is powered, and the heart H is now driven to beat at an elevated rate, which not only makes its beating much more regular (i.e., at a precise frequency) but also prevents "twitchy" reactions by the heart muscle, which could cause an error in the operation.

Pacing results from the platform oscillation $O_P$ activating the switch 40, which sends a trigger signal to the pace circuit 74, which stimulates the heart H once for each trigger signal, i.e., at the frequency of switch triggering. The invention optionally includes an adjustable delay circuit 76 between the switch 40 and pace circuit, as illustrated schematically by a hand 78 and a knob 80 on the delay box 76. The delay adjust may be either mechanical or electronic.

The platform includes a capacitor plate 21, also seen in FIGS. 1 and 3. If the platform 20 is metallic, the plate may optionally comprise the entire platform. The plate 21 forms one side of a capacitor with the heart H, which preferably is grounded either through the chest C and patient supports or by an electrode (not shown). The capacitance value of the capacitor formed by the heart H and plate 21 is a function of the distance between them.

An audio oscillator 82, such as a grid-dip oscillator, is used to generate a frequency that is a function of the capacitance; this frequency is amplified by an amplifier 84 and turned into an audible tone by a transducer L; the tone is heard by the ear E of the surgeon. The surgeon can detect any mis-match between the platform oscillation $O_P$ and the heart oscillation $O_H$ by listening to the tone, because when the oscillations are different the distance will vary and the tone will warble. This provides feedback on the synchronization, phase locking, and amplitude differences of the platform oscillation $O_P$ and the heart oscillation $O_H$.

A difference in amplitude will cause a regular pitch variation at the common frequency of the heart and platform. The surgeon adjusts the position of the slider 33 (FIG. 2) by driving the motor 17 one way and another, to turn the threaded rod 37 clockwise and counter-clockwise until the tone variation is minimized, as illustrated by hand 86 and control knob 88. Then the surgeon might also adjust the phase of the heart and platform oscillations $O_H$ and $O_P$ with the pacing trigger delay 76 to further reduce warble.

If the tone changes slowly over a number of beats, this indicates that the heart H is not following the pacer or the pacer is not following the trigger signals.

The tone also provides feedback about the shape of the cam, since if the profile is not correct then warble will be heard (even if there is no mis-match in frequency, phase, or amplitude) because of differences in the oscillation patterns. If the profile is adjustable, then the surgeon can adjust this as well.

When the tone variation is stable and adjusted to minimum variation, then the surgeon is ready to operate.

The invention includes variations on the preferred embodiment described above.

The present invention allows a surgeon or veterinarian to operate on any moving organ, and the operation is not limited to the surface. The invention permits canceling of relative motion between a platform and an exterior or interior portion of a beating heart or any other organ. A surface is of course only one particular type of portion of an organ.

To reduce the capacitive effect of the other body parts and the effects of breathing, peristalsis, and other motions, the platform capacitor plate 21 can alternatively be made as an insulated, discrete conductor placed on an extended member, so that the capacitor plate 21 is quite close to the heart H. This increases the heart-plate capacitance while reducing the "stray" capacitance due to other organs or objects.

Figure 6:
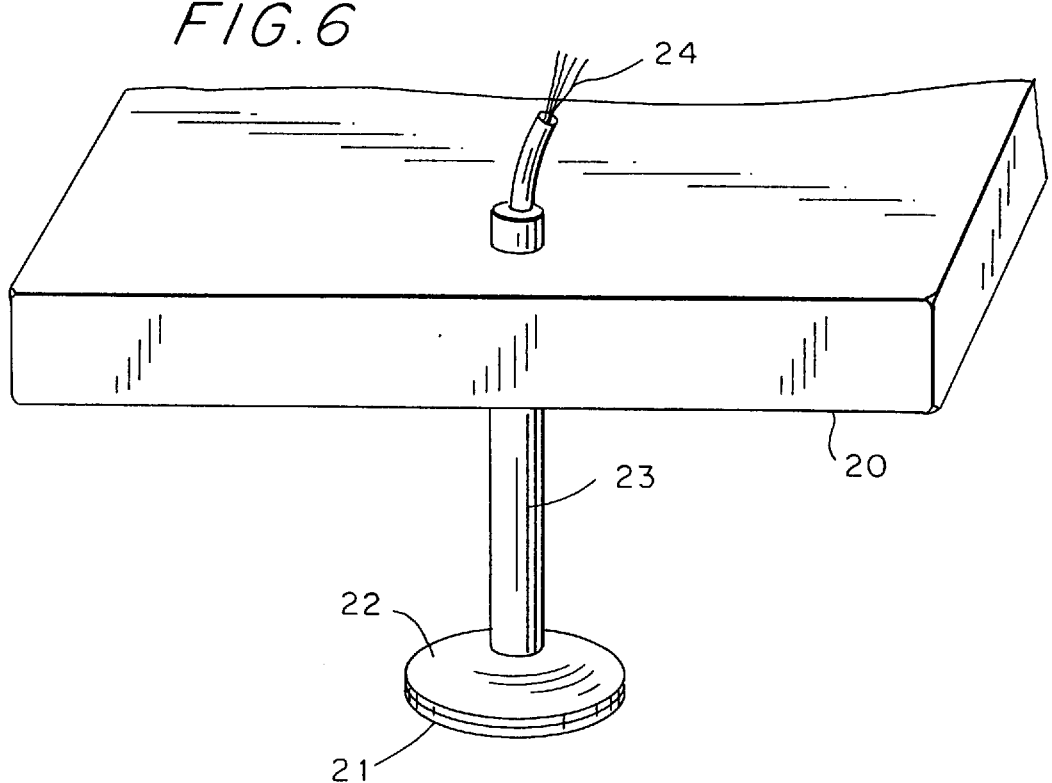
FIG. 6 is a perspective view of an alternate capacitor plate.

An example is shown in FIG. 6. The capacitive electrode 21 is disposed at the bottom of a stalk 23 descending from the platform 20, with an optional electrode support 22. The stalk 23 may be adjustable to vary the protruding length for different chosen heart-platform distances. The electrode 21 is coupled to a capacitor wire 24, which may include a grounded shield (not shown) to minimize hand capacitance, especially where the platform 20 is non-metallic.

The platform capacitor plate 21 can also be a hand-held device to compensate for any hand jitter or flailing when adjusting the motion. Both the laser 55 and the capacitor plate can employ the same clip or other attachment at the end of the platform.

The adjustments which the surgeon makes to the platform oscillation phase and amplitude can also be made by automatic equipment that senses the capacitance variations and adjusts the platform motion accordingly.

The invention also includes means for manually or automatically augmenting the cam motion or modifying the cam profile. The latter can be accomplished with a cam whose cross section varies along the rotation axis.

The present invention also contemplates feedback means for maintaining a constant distance between the platform and the portion of the heart. With this feedback the output of a heart-platform distance sensor acts as a signal to correct an actuator which automatically maintains the distance. This arrangement will compensate for any difference in pattern between the cam-driven platform oscillation and the heard oscillation related to the particular heart portion being operated on, individual variation, heart disease or malformation, and so on. The feedback loop arrangement will also compensate for breathing, unexpected sudden movements by the patient or surgeon, or accidental jarring of the patient or gear.

This distance-correcting feedback arrangement preferably augments the mechanical drive for the platform (or operating part of an instrument), rather than replacing it. Augmentation is better because the feedback arrangement has less work to do (i.e., smaller excursions to compensate for) than if it were relied upon to drive the platform by itself; and failure of the feedback loop will not endanger the patient.

In such an arrangement either the capacitance or some other distance measure can also be used to directly drive an actuator (in place of the rotating cam) through a simple feedback circuit. For example, an oscillation frequency which is a function of capacitance (i.e. heart-electrode distance) can be detected by a conventional unit whose output signal is a measure of the frequency, and thus of the distance. Such a signal can be amplified and used to directly drive a quick-acting actuator. Alternatively, the frequency can be compared to a standard frequency, either by comparing unit output signals or by beating the input oscillation signals together and detecting the beat frequency in one unit. In the later setup the standard frequency could be adjusted to vary the platform-heart distance. These various embodiments, and all other means for causing reciprocation of the platform, are within the scope of the following claims.

Dual opposed counter-acting actuators (or a double-acting single actuator) may be used in the invention if the heart surface motion is at such an angle to the vertical, or the downward acceleration is too quick, such that the platform does not fall fast enough to keep up with the heart. The additional downward actuator in this case would push the platform toward the heart as needed.

In one embodiment, the feedback loop can include a pattern-remembering computer which will "learn" the deviations between the heart and platform that recur in every cycle and anticipate them; this will result in greater accuracy.

The heart-platform distance sensor can optionally be the capacitive plate 21, especially if the plate is projected outward and down from the end of the platform to be adjacent the portion of the heart H that is to be operated on. The sensor alternatively can rely on well known sonar or radar distance measuring techniques.

Figure 7:
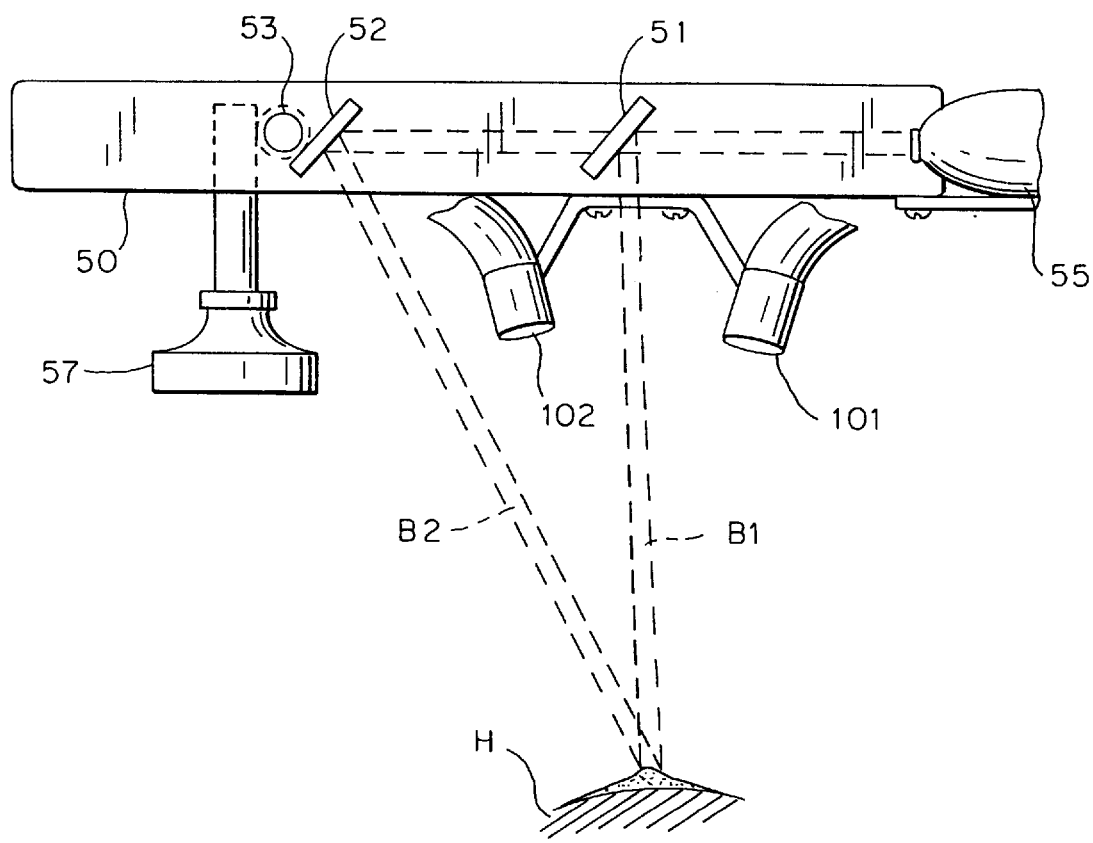
FIG. 7 is an elevational view of an embodiment with cameras and a split laser beam.

FIG. 7 shows an alternative embodiment of the platform 20 in which the laser alignment is modified and TV imaging is included.

The beam from the laser 55 is split by a partly-silvered fixed mirror 51 into two beams El and B2. Beam B2 is deflected by a second, totally-reflecting mirror 52, which may be angle-adjustable by mounting 53 and control knob 57.

Preferably, the fixed beam BE is aligned to the platform motion. The two beams converge at the heart H surface. This provides a distance check when the platform is oscillating, since any deviation will be apparent from the appearance of two laser spots from one, or relative motion of two adjacent spots.

The invention may include means for the second beam B2 to be selectively blocked or deflected so that the beam B1 can be used alone, as discussed above.

The beam apparatus alternatively may be emplaced on the platform 20 rather than on the clamp member 50 (not shown). The platform can include an end indentation or working hole for the surgeon to operate through (not shown), with the beams converging from either side. Especially in this case the laser 55 may be located near the hinge 12 with the beam B extending generally along (or in) the platform, with a beam splitter, prisms, mirrors and other elements as needed arranged to deflect the beams downward with or without adjustment.

TV viewers 101 and 102 are preferably fiber-optic imaging devices of the type used in endoscopes, which send images through fiber bundles to remote cameras (e.g., CCD camera) which generate electronic TV signals for display on a TV monitor (not shown) and/or to an optical viewing device (not shown).

Preferably, the surgeon watches the heart H through a binocular device using images from both viewers 101 and 102 for stereo vision with depth perception. These elements are conventional. One of the images many also be projected onto the TV monitor for additional viewing by technicians and assisting surgeons. Such an arrangement has the advantage that a technician can attend to the adjusting and monitoring the heart-platform distance and/or the platform oscillation $O_P$ while the surgeon concentrates on operating. The technician would require only one TV image on a regular monitor; the surgeon could advantageously use stereo imaging.

The TV cameras 101 and 102 may optionally be angularly-adjustable for improved stereo imaging at different heart-platform distances which may be chosen by the surgeon, and the angle adjustment may be coupled to the laser beam angle adjustment. The TV cameras and laser beams may be aligned and made adjustable by a single mechanism.

An additional TV camera (not shown) could be placed to one side, e.g. to the left in FIG. 7 looking horizontally at the heart H and platform 20. This TV image could be used for teaching, additional viewing, or calibrating the heart-platform distance according to a desired distance and a known scale of the TV image on a monitor. Preferably, this miniature camera is fixed so as to oscillate with the platform and is directed at the site of anastomosis. As the oscillation of the camera, fixed with respect to the oscillating platform, in synchronized with the oscillation of the surface of the heart, the image will be stabilized. Thus, the surgeon can simply view the monitor, rather than the oscillating heart surface itself, to see the anastomosis site substantially still, thereby allowing the delicate surgical procedure to proceed as if the heart and the surgeon's hand were not oscillating.

The present invention also contemplates that the moving platform 20 includes instruments mounted near the end of the platform adjacent the hear, which can be manipulated by the surgeon via remote control. Examples would be actuators mounted on the platform 20 and driven by electric signals, pressure, or mechanical means (wires, linkages, etc.), and other conventional manipulators; surgical implements pivoted on the platform 20; and/or guides or rests for surgical implements, e.g. minature oar-lock type devices, notches, and so on.

A lamp (not shown) may optionally be mounted on the apparatus of the invention for illumination. A focussing adjustment for the viewers 101 and 102 may be provided (not shown).

The claimed "means for supporting a surgical tool" is intended to comprehend the illustrated platform 20 as well as any functional equivalent thereof. For example, the platform may be flat as illustrated or it may be molded or otherwise shaped so as to conform to the shape of the surgeon's arm and/or wrist and may optionally be cushioned. It may be made of any rigid material. Other means for supporting the arm are not excluded, including a support which fastens to the arm from above.

While the "surgical tool" to which the present invention is predominantly directed is the surgeon's arm and hand, the present invention is intended to include a support for other types of surgical tools, such as remotely operated devices, a laser or optics for a laser intended for surgical operation on an oscillating organ, etc. As long as there is motivation to eliminate relative motion between a tool of any kind and an oscillating organ in a surgical setting, the apparatus of the present invention may be used.

The "means for positioning" of the present claims is intended to encompass the support apparatus illustrated in FIG. 4, as well as all other constructions which will permit the positioning of the platform relative to the oscillating organ. Thus, while a simple photographic or telescope tripod arrangement is preferred, more complicated and precise apparatus may also be used. Those of ordinary skill in the art can readily develop or adapt from other arts a myriad of different devices which will allow the placement of the platform to be carefully adjusted with respect to the distance from the point of operation on the oscillating organ, such as the target of anastomosis on a beating heart, as well as the various angular adjustments thereof. The positioning means must be strong enough to support the oscillating platform and the surgeon's arm or other surgical tool thereon without extraneous movement.

The "means for causing reciprocation" is intended to encompass the disclosed mechanism, including the cam 30 as described herein, as well as all other mechanisms which will permit such reciprocation and are thus functionally equivalent to such a cam. Thus, once the intended function is known to those of ordinary skill in the art, many other mechanisms to accomplish the function can be designed and are intended to be part of the present invention. For example, the reciprocation may be caused by a piston driven by a computer so as to cause the platform or other means for supporting to oscillate at a predetermined programmed rate. Sensors to determine the relative amplitude, angle and pattern of the platform as compared to the oscillating organ could feed input to the computer which would then feed back adjustments to the piston. While the illustrated means is simple and presently preferred, any other mechanism for accomplishing the specified function must be considered to be a functional equivalent to the illustrated cam.

The "means for synchronizing" the reciprocation of the pacer with the oscillation of the platform is preferably the illustrated switch 40 triggered by the actual movement of the support. Again, however, any other mechanism for accomplishing this function is intended to be an equivalent to the illustrated mechanism. Thus, for example, if the movement of the platform is computer controlled, the computer can also output the pacing signal. It is preferred that the same mechanism which drives the oscillation of the platform effectively drives the pacing of the heart.

The claimed means for adjusting one or more of the amplitude, phase or pattern of the oscillation of the platform is intended to encompass not only the illustrated mechanisms, but anything else that may be devised in order to accomplish this function. While a capacitance system for generating an auditory signal which varies as the distance varies, but becomes constant as the amplitude comes into alignment, is a simple and effective means for accomplishing this function, those of ordinary skill in the art can readily develop other means for accomplishing this function which are intended to be equivalent to the auditory mechanism disclosed. Thus, in a more complex computer driven system, the distance between the platform and the oscillating organ may be measured by other means, such as radar, sonar or laser type signals which display the relative distances on a computer output with the computer using this signal to adjust the amplitude of oscillation to maintain the distance constant.

With respect to the means for indicating the degree of alignment or non-alignment of the direction of oscillation of the platform with the direction of oscillation of the moving organ, this element is intended to include not only the laser pointer device illustrated, but any other mechanism that may be developed by one of ordinary skill in the art to accomplish this function. While the use of a laser pointer is simple and elegant in allowing the surgeon to see when angular alignment is proper by the appearance of only a point on the surface of the moving organ rather than a short line, other more complicated methods may be designed which are intended to be equivalent to such a laser pointer, as long as the intended function is accomplished. Again, automatic measurement of alignment by any number of sensing means can be fed into a computer which controls the direction of oscillation to cause it to correspond to the direction of oscillation of the organ.

The industrial applicability is in medical devices. The problem solved by the invention is motion of a moving organ to be operated on. The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. An apparatus for supporting a surgical tool during a surgical operation on an organ moving in oscillation, comprising in combination:

means for supporting a surgical tool;

means for positioning said means for supporting adjacent the oscillating organ; and means for causing reciprocation of said means for supporting in a platform oscillation which is in synchronicity with the oscillation of the moving organ, wherein relative motion between the oscillating organ and the means for supporting is at least partially canceled.

2. An apparatus in accordance with claim 1, wherein the oscillating organ is a heart and further including a means for pacing the heart to beat in a constant rhythm and means for synchrony of the reciprocation of said means for supporting and the means for pacing such that the means for supporting and the paced-heart oscillate in synchrony.

3. An apparatus in accordance with claim 1, further including means for adjusting one or more of the amplitude, phase or pattern of the oscillation of said means for supporting to correspond to the amplitude of the oscillation of the moving organ.

4. An apparatus in accordance with claim 3, wherein said means for adjusting further includes means for sensing the relative amplitudes of oscillation of said means for supporting and the organ.

5. An apparatus in accordance with claim 4, wherein said means for adjusting includes means for indicating the degree of difference between the oscillations of the said means for supporting and the organ.

6. An apparatus in accordance with claim 1, further including means for indicating the degree of alignment or non-alignment of the direction of oscillation of said means for supporting with the direction of oscillation of the moving organ.

7. An apparatus in accordance with claim 1, wherein the surgical tool is a human hand on the arm of the person conducting the surgical operation and said means for supporting comprises a platform for supporting said arm.

8. An apparatus in accordance with claim 2, wherein said means for pacing is triggered by the oscillation of said means for supporting.

9. An apparatus in accordance with claim 1, wherein said means for causing reciprocation comprises a rotary cam having a profile adapted to the pattern of the organ oscillation.

10. An apparatus in accordance with claim 3, wherein said means for supporting comprises a platform coupled to said means for positioning by a hinge, said means for causing reciprocation comprises a rotary cam having a profile adapted to the pattern of the organ oscillation, and said means for adjusting comprises means for moving said cam toward and away from said hinge.

11. An apparatus in accordance with claim 4, wherein said means for sensing includes a capacitor plate connected to said means for supporting.

12. The apparatus according to claim 3, wherein said means for adjusting include means for outputting a signal representative of the distance between the said organ and the means for supporting.

13. The apparatus according to claim 12, wherein said means for outputting includes a capacitor plate on said means for supporting adjacent the oscillating organ.

14. The apparatus according to claim 12, wherein said means for adjusting adjusts the oscillation of said means for supporting according to the signal output by said means for outputting.

15. The apparatus according to claim 14, wherein said means for adjusting causes adjustment of the oscillation amplitude of said means for supporting.

16. The apparatus according to claim 14, wherein said means for adjusting causes adjustment of the oscillation phase of said means for supporting.

17. The apparatus according to claim 14, wherein said means for adjusting causes adjustment of the oscillation pattern of said means for supporting.

18. The apparatus according to claim 5, wherein said means for indicating comprises an auditory signal generally proportional to the distance signal.

19. An apparatus in accordance with claim 1, wherein the point on the oscillating organ at which the surgical operation is intended to be performed oscillates in a line comprising a direction of oscillation and wherein said means for positioning includes means for angularly adjusting the means for supporting so as to align with the direction of oscillation of the oscillating organ.

20. An apparatus in accordance with claim 19, wherein said means for angularly adjusting includes means for indicating when the direction of oscillation of the means for supporting is aligned with the direction of indication of the oscillating organ.

21. An apparatus in accordance with claim 20, wherein said means for indicating alignment includes a laser.

22. An apparatus in accordance with claim 2, wherein said means for synchronizing includes means for triggering a pacing circuit according to the oscillation of said means for supporting.

23. An apparatus in accordance with claim 22, including means for adjusting the means for triggering relative to the phase of the oscillation of said means for supporting.

24. An apparatus in accordance with claim 2, wherein said means for pacing causes the heart to beat faster than it would if not paced.

25. A device facilitating work by a human hand on a surface moving in a surface motion, the device comprising:
   a hand-supporting platform;
   means for positioning said platform adjacent the surface; and
   means for producing a platform motion substantially matching the surface motion;
   whereby relative motion between the platform and the surface is substantially reduced.

26. The device according to claim 25, wherein the means for producing a platform motion includes a surface-platform distance sensor and a platform actuator.

27. The device according to claim 26, comprising means coupled to the distance sensor for outputting an auditory signal generally proportional to the distance between the platform and the surface.

28. The device according to claim 25, further comprising means for angular adjustment of the platform and of means for indicating whether or not the platform motion and the surface motion are in angular alignment.

* * * * *